US012767765B2

(12) United States Patent
Baumgartner et al.

(10) Patent No.: US 12,767,765 B2
(45) Date of Patent: Oct. 20, 2026

(54) SILICONE ELASTOMER FROM SILYLATED POLYSACCHARIDES

(71) Applicants: Dow Silicones Corporation, Midland, MI (US); Rohm and Haas Company, Collegeville, PA (US)

(72) Inventors: Ryan Baumgartner, Midland, MI (US); Shane Mangold, Midland, MI (US); Zachary Wenzlick, Midland, MI (US); Marc-Andre Courtemanche, Midland, MI (US); Roxanne Haller, Saginaw, MI (US); Michael Ferritto, Midland, MI (US); Gregoire Cardoen, Collegeville, PA (US)

(73) Assignees: Dow Silicones Corporation, Midland, MI (US); Rohm and Haas Company, Collegeville, PA (US)

( * ) Notice: Subject to any disclaimer, the term of this patent is extended or adjusted under 35 U.S.C. 154(b) by 510 days.

(21) Appl. No.: 18/261,018

(22) PCT Filed: Feb. 24, 2022

(86) PCT No.: PCT/US2022/017667

§ 371 (c)(1),
(2) Date: Jul. 11, 2023

(87) PCT Pub. No.: WO2022/203801

PCT Pub. Date: Sep. 29, 2022

(65) Prior Publication Data

US 2024/0110014 A1 Apr. 4, 2024

Related U.S. Application Data

(60) Provisional application No. 63/163,969, filed on Mar. 22, 2021.

(51) Int. Cl.

| | |
|---|---|
| ***C08G 77/42*** | (2006.01) |
| ***A61K 8/73*** | (2006.01) |
| ***A61K 8/89*** | (2006.01) |
| ***A61Q 19/00*** | (2006.01) |
| ***C08B 37/00*** | (2006.01) |
| ***C08G 77/08*** | (2006.01) |
| ***C08G 77/12*** | (2006.01) |
| ***C08G 77/20*** | (2006.01) |
| ***C08L 5/00*** | (2006.01) |
| ***C08L 5/02*** | (2006.01) |
| ***C08L 5/16*** | (2006.01) |
| ***C08L 83/04*** | (2006.01) |

(52) U.S. Cl.

CPC ............. *C08G 77/42* (2013.01); *A61K 8/738* (2013.01); *A61K 8/89* (2013.01); *A61Q 19/00* (2013.01); *C08B 37/00* (2013.01); *C08G 77/08* (2013.01); *C08G 77/12* (2013.01); *C08G 77/20* (2013.01); *C08L 5/00* (2013.01); *C08L 5/02* (2013.01); *C08L 5/16* (2013.01); *C08L 83/04* (2013.01); *A61K 2800/48* (2013.01); *A61K 2800/95* (2013.01)

(58) Field of Classification Search

CPC ........ C08G 77/42; C08G 77/08; C08G 77/12; A61K 8/738; A61K 8/89; A61K 2800/48; A61K 2800/95; A61Q 19/00; C08L 5/02; C08L 5/16; C08L 5/00; C08B 37/00

See application file for complete search history.

(56) References Cited

U.S. PATENT DOCUMENTS

| | | | |
|---|---|---|---|
| 5,025,073 | A | 6/1991 | Lewis et al. |
| 5,403,898 | A | 4/1995 | Bradshaw et al. |
| 5,498,703 | A | 3/1996 | O'Lenick, Jr. |
| 5,831,080 | A | 11/1998 | Sejpka et al. |
| 6,372,020 | B2 | 4/2002 | Hong et al. |
| 6,703,497 | B1 | 3/2004 | Ladouce et al. |
| 7,235,186 | B2 | 6/2007 | Ochs et al. |
| 10,053,543 | B2 | 8/2018 | Knoer |
| 2016/0311980 | A1 | 10/2016 | Knoer |
| 2018/0282438 | A1 | 10/2018 | Mukai et al. |

FOREIGN PATENT DOCUMENTS

| | | |
|---|---|---|
| CN | 107880089 | 4/2018 |
| JP | 5528648 | 6/2014 |
| WO | 2014182907 | 11/2014 |
| WO | 2020139403 | 7/2020 |
| WO | 2020139404 | 7/2020 |

OTHER PUBLICATIONS

Preparation and Characterization of Organic-Inorganic Hybrids Translation (Year: 1994).*
Preparation et Chracterization Des Hybrides Organiques-Inorganiques (Year: 1994).*
Ali, "Cyclodextrin-polymethylhydrosiloxane gel as sensitive membrane for heavy ion sensors", Materials Science and Engineering C, Elsevier Science S.A., 1998, pp. 53-58, vol. 6, No. 1.
Fischer, "Permethyl-?-cyclodextrin, Chemically Bonded to Polysiloxane: a Chiral Stationary Phase with Wider Application Range for Enantiomer Separation by Capillary Gas Chromatography", Angew. Chem. Int. Ed. Engl., 1990, pp. 427-429, vol. 29, No. 4.
Harabagiu, "Synthesis and characterization of persilylated cyclodextrins", Carbohydrate Polymers, 2004, pp. 301-311, vol. 56, No. 3.
Stiubianu, "Chemical modification of cellulose acetate by allylation and crosslinking with siloxane derivatives", Polym. Int., 2012, pp. 1115-1126, vol. 61.

* cited by examiner

*Primary Examiner* — Marc S Zimmer
*Assistant Examiner* — Virginia L Stonehocker
(74) *Attorney, Agent, or Firm* — Steven W. Mork

(57) ABSTRACT

A composition includes a crosslinked polysiloxane elastomer with 2 or more carbon-oxygen-silicon linkages between a polysaccharide component and polysiloxane component, where the polysaccharide component is other than a cellulose or starch component.

9 Claims, No Drawings

SILICONE ELASTOMER FROM SILYLATED POLYSACCHARIDES

FIELD OF THE INVENTION

The present invention relates to silicone elastomers, gels comprising silicone elastomers and pastes made from gels comprising silicone elastomers.

INTRODUCTION

Polysiloxane elastomer materials have been desirable in the cosmetic industry to thicken carrier fluids while imparting desirable sensory properties to cosmetics, especially in the area of feel and touch on skin-based cosmetics to the mixture of elastomer and carrier fluid. Polysiloxane elastomers are crosslinked gel materials that can impart a smooth, dry, powdery feel desirable in many cosmetics while also thickening carrier fluids. Bio-renewable and/or bio-sourced materials are desirable for many uses, including for use in the cosmetic industry. Combining a bio-renewable and/or bio-sourced aspect to polysiloxane-based elastomer materials while still achieving thickening and sensory aspects associated with the polysiloxane elastomers would be one way to advance the field of polysiloxane elastomers, particularly for use in cosmetics.

Moreover, it is desirable for the polysiloxane-based elastomer to comprise a bio-renewable and/or bio-sourced component linked to the polysiloxane component through a carbon-oxygen-silicon (C—O—Si) bond linkage rather than a carbon-oxygen-carbon (C—O—C) bond linkage. C—O—Si linkages are less hydrolytically stable than C—O—C linkage, which causes molecules with C—O—Si linkages more degradable and environmentally friendly. Additionally, alkoxylated materials with C—O—C bond linkages can carry with them trace level of 1,4-dioxane, which is an undesirable contaminate particularly in a cosmetic material.

Cosmetics are applied to the skin, yet skin is often subject to exposure to moisture and even washing such as washing hands. It is desirable to identify elastomer gels with organic solvent that can be processed into a paste with desirable sensory properties that is wash-resistant (durable) so that it will have a greater tendency to remain on a surface such as skin despite being exposed to rinsing or washing.

It is desirable for a polysiloxane-based elastomer to be highly compatible in a variety of organic solvents to allow use of the elastomer as a thickening agent (gelling agent) in formulations with a variety of different organic solvent carrier fluids. An elastomer is compatible with an organic solvent if they can form a gel with the solvent that is more viscous than the solvent alone. Even more, it is desirable for a gel of the elastomer and solvent to be able to form a paste that is compatible with solvent by forming a homogeneous mixture, preferably that is translucent or even transparent to visible light, and that is stable to phase separation.

Even more, it is desirable to identify a way to prepare polysiloxane elastomers using a hydrosilylation reaction, but without yellowing or coloring of the reaction product. Hydrosilylation reactions typically use a platinum-based catalyst. The platinum-based catalyst often results in formation of a yellow color to the reaction product. It would be desirable to avoid that yellowing color, particularly in cosmetic applications.

BRIEF SUMMARY OF THE INVENTION

The present invention provides a polysiloxane-based elastomer that thickens carrier fluids while imparting desirable smooth, dry, powdery feel to a mixture of the carrier fluid and elastomer. The polysiloxane-based elastomer comprises a polysaccharide component, which is a bio-renewable and/or bio-sourced component. Moreover, the polysiloxane-based elastomer of the present invention connects the polysaccharide component to the polysiloxane component through a C—O—Si linkage. In particular, the polysaccharide component is connected to polysiloxane components through at least two C—O—Si linkages with the polysiloxane component serving as a crosslinked component in the polysiloxane-based elastomer. Yet further, the present invention provides such a polysiloxane-based elastomer that gels a variety of organic solvents and that can be formulated into a paste that has greater wash resistance (durability) than other polysiloxane elastomers. The polysiloxane-based elastomer of the present invention tends to be highly compatible with a variety of organic solvents in that the polysiloxane-based elastomer forms a mixture with an organic solvent carrier fluid that is more viscous than the carrier fluid and that can be formed into a paste that is homogeneous, translucent or transparent to visible light, and stable to phase separation. The polysiloxane-based elastomer is made by a hydrosilylation reaction that can surprisingly demonstrate minimal yellowing (less than 300, even less than 100 on the APHA coloring scale).

The present invention is partly a result of discovering how to prepare a polysaccharide intermediate having alkenyl functionality attached to the polysaccharide through C—O—Si linkages. This alkenyl functional polysaccharide was found to react with SiH functional polysiloxanes to provide a polysiloxane elastomer gel with the aforementioned desired properties.

In a first aspect, the present invention is a composition comprising a crosslinked polysiloxane elastomer comprising 2 or more carbon-oxygen-silicon linkages between a polysaccharide component and polysiloxane component, where the polysaccharide component is other than a cellulose or starch component.

In a second aspect, the present invention is a method for preparing the composition of the first aspect, the method comprising forming the crosslinked polysiloxane elastomer by a hydrosilylation addition reaction between reactants comprising: (a) a SiH functional Polyorganosiloxane; (b) an alkenyl-functional polysaccharide that is characterized by: (i) comprising linked fructose, galactose, anhydrogalactose, or glucose saccharide units provided that glycosidic linkages of glucose are alpha linkages; and (ii) on average one to 100 mole-percent of the hydroxyl groups on the alkenyl-function polysaccharide have been silylated with a silyl group having the structure —$SiR_3$ linked to the polysaccharide through a C—O—Si bond where each R is independently selected from hydrocarbyl radicals having from one to 12 carbon atoms, provided that on average at least 2.0 R groups per polysaccharide are terminal alkenyl groups; and (iii) at the alkenyl-functional polysaccharide is other than a silylated starch; and optionally (c) additional crosslinking additives; the reaction being run in the presence of: (d) a platinum-based hydrosilylation catalyst; and (e) a solvent.

The elastomer of the present invention is useful as an additive for cosmetics to achieve desired sensory character to the cosmetic, especially to achieve a smooth, dry, powdery feel.

DETAILED DESCRIPTION OF THE INVENTION

Test methods refer to the most recent test method as of the priority date of this document when a date is not indicated with the test method number. References to test methods contain both a reference to the testing society and the test method number. The following test method abbreviations and identifiers apply herein: ASTM refers to ASTM International methods; END refers to European Norm; DIN refers to Deutsches Institut für Normung; ISO refers to International Organization for Standards; and UL refers to Underwriters Laboratory.

Products identified by their tradename refer to the compositions available under those tradenames on the priority date of this document.

"Multiple" means two or more. "And/or" means "and, or as an alternative". All ranges include endpoints unless otherwise indicated.

"Hydrocarbyl" refers to a univalent group formed by removing a hydrogen atom from a hydrocarbon and includes alkyl and aryl groups.

"Alkyl" refers to a hydrocarbon radical derivable from an alkane by removal of a hydrogen atom. An alkyl can be linear or branched.

"Aryl" refers to a radical formable by removing a hydrogen atom from an aromatic hydrocarbon.

"Polysaccharide" refers to a molecule comprising 2 or more saccharide units that are covalently bonded together. "Polysaccharide" includes what is sometimes referred to as a "disaccharide" and "oligosaccharide". A "disaccharide" is a molecule comprising 2 saccharide units that are covalently bonded together. An "oligosaccharide" is a molecule comprising from 3 to 10 saccharide units covalently bonded in a chain, which can be a cyclical chain.

"Pendant groups", with respect to polysaccharides, refer to groups other than hydrogen extending off from a polysaccharide backbone, specifically from a carbon atom on a pyranose or furanose ring of a polysaccharide backbone. Adjoining saccharide groups in a polysaccharide are not considered "pendant groups" but rather part of the polysaccharide backbone.

"Starch" refers to a combination of amylose and amylopectin.

"APHA" refers to American Public Health Association.

"Terminal alkenyl" refers to a univalent aliphatic hydrocarbon radical derivable from an alkene having a carbon-carbon double bond (C═C) where a carbon atom of the C═C is a terminal carbon and where the univalent aliphatic hydrocarbon radical is derivable by removing one hydrogen atom from a carbon atom other than the terminal carbon atom in the C═C.

The present invention is a composition comprising a crosslinked polysiloxane elastomer comprising 2 or more carbon-oxygen-silicon (C—O—Si) linkages between a polysaccharide component and a polysiloxane component. An elastomer is a crosslinked polymer that has elastic properties, which means it is not so heavily crosslinked that it is a rigid material but is sufficiently crosslinked so as to be insoluble in a solvent. In fact, the elastomer actually swells with solvent to form a gel instead of dissolving in solvent. That is one of the features of the elastomer of the present invention is that it is capable of thickening solvents even to the point of being non-flowable gel at 25 degrees Celsius (° C.) while also being able to be processed (for example, gelled in solvent and then subjected to shear mixing) to form a paste having desirable sensory aspects such as a smooth, dry, powdery feel for the resulting thickened material that is comparable to current polysiloxane additives used for achieving such desirably sensory characteristics.

The crosslinked polysiloxane elastomer comprises polysaccharide-based crosslinking agents that interconnect with polysiloxane segments through C—O—Si linkages. The carbon of the C—O—Si linkage is desirably a carbon of the hexose of a polysaccharide. Typically, the silicon atom of the C—O—Si linkage is further linked to a silicon atom of a polysiloxane through a divalent hydrocarbyl that has 2 or more, and can have 3 or more, 4 or more, 5 or more even 6 or more while at the same time typically has 12 or fewer, usually 10 or fewer, 8 or fewer, 6 or fewer, 4 or fewer, even 3 or fewer carbon atoms. For example, the divalent hydrocarbyl can be linear having the general chemical formula $-(CH_2)$, where n is the number of carbon atoms in the divalent hydrocarbyl. A common divalent hydrocarbyl for the present crosslinked polysiloxane has two carbon atoms. The C—O—Si linkage and divalent hydrocarbyl link between the Si of the C—O—Si and a polysiloxane component is a characteristic feature of the unique way the crosslinked polysiloxane elastomer of the present invention is made. In particular, the crosslinked polysiloxane elastomer is made with a hydrosilylation reaction between an SiH functional polysiloxane and a polysaccharide intermediate having two or more $C—O—SiR_3$ groups, where each R is independently selected from hydrocarbyl radicals having from one to 12 carbon atoms, provided that on average at least one R per polysaccharide has a terminally unsaturated carbon-carbon double bond. Preferably, and typically, the carbon of the $C—O—SiR_3$ group is a carbon of the hexose of the polysaccharide. The hydrosilylation reaction involves a reaction between the terminally unsaturated carbon-carbon double bond (C═C) of the $C—O—SiR_3$ group and the SiH group of the polysiloxane resulting in the residual R group that comprised the C═C to serve as the divalent carbon linking the C—O—Si linkage and the polysiloxane. Notably, the linkage between the saccharide and siloxane can be free of any one or any combination of more than one functionality selected from ethers, esters, urethanes and ureas.

The polysaccharide of the crosslinked polysiloxane elastomer is other than a cellulose component or a starch component. It has been discovered that the polysaccharide intermediate used to make the elastomer of the present invention is not soluble in non-polar aromatic solvents when the saccharide component is cellulose or starch. Insolubility in non-polar aromatic solvents makes the polysaccharide intermediate less versatile and limits what solvents can be used to make the crosslinked polysiloxane elastomer.

Desirably, the polysaccharide component of the crosslinked polysiloxane elastomer comprises fructose, galactose, anhydrogalactose or glucose linked saccharide units provided that glycosidic linkages of glucose are alpha linkages. The polysaccharide component of the crosslinked polysiloxane elastomer desirably only has pendant groups other than the linkage to the polysiloxane that are selected from a group consisting of $—OSiR_3$ groups, $—CH_2OSiR_3$ groups, —OH and $—CH_2OH$. Typically, the polysaccharide component comprises on average 2 to 2000 linked saccharide units. The polysaccharide can comprise 2 or more, 3 or more, 4 or more, 5 or more, 6 or more, 7 or more, 8 or more, 9 or more, 10 or more, 20 or more, 40 or more, 60 or more, 80 or more, even 100 or more, or 200 or more while at the same time typically comprise 2000 or fewer, 1800 or fewer, 1600 or fewer, 1400 or fewer, 1200 or fewer, 1000 or fewer, 800 or fewer, 600 or fewer, 400 or fewer, 200 or fewer, 100 or fewer, 80 or fewer, 60 or fewer, 40 or fewer, 20 or fewer, or even 10 of fewer saccharide units per molecule. Determine the average number of saccharide units per molecule in the polysaccharide component from the polysaccharide starting material used to make the crosslinked polysiloxane elastomer. The number of saccharide units in the polysaccharide used to make the crosslinked polysiloxane elastomer can be determined either from the supplier, from common knowledge in the art as to how many saccharide units the particular polysaccharide contains or if neither of these are possible, by gel permeation chromatography using standard techniques.

The polysiloxane component of the crosslinked polysiloxane elastomer is crosslinked through the polysaccharide groups. The extent of crosslinking should be sufficient to achieve gelling in the presence of solvent. The polysiloxane component can be linear, branched or cyclic. Generally, the polysiloxane component comprises one or any combination of polysiloxane units selected from $R_3SiO_{1/2}$ ("M"-type units), $R_2SiO_{2/2}$ ("D"-type units), $RSiO_{3/2}$ ("T"-type units) and $SiO_{4/2}$ ("Q"-type units), where each R is independently selected from hydrogen, hydrocarbyl and substituted hydrocarbyl groups and the oxygen atoms listed in the units refer to oxygens bonded to silicon atoms of two different siloxane units with the subscript on the oxygen referring to the number of shared oxygens in the numerator and designates the oxygen atom is shared with another siloxane unit by dividing the numerator by 2. Desirably, the polysiloxane component is linear comprising M-type and D-type polysiloxane units and has a degree of polymerization of zero or more, one or more, 2 or more, 3 or more, 4 or more, 5 or more, 6 or more, 7 or more, 8 or more, 9 or more, 10 or more, 15 or more, 20 or more, 30 or more, 40 or more, 50 or more, 75 or more, 100 or more, even 150 or more and most desirably 200 or less, and can be 150 or less, 100 or less, 75 or less, 50 or less, 40 or less, 30 or less, 20 or less, even 10 or less where degree of polymerization is the number of D-type units in the polysiloxane. If the linear polysiloxane exceeds a DP of 200 the resulting elastomer tends to be weak and pliable as a gel. Most desirably, the DP is 20 or less, preferably 15 or less or even lower in order to maximize the concentration of biorenewable polysaccharide component in the crosslinked polysiloxane elastomer.

The crosslinked polysiloxane elastomer typically comprises one wt % or more, 5 wt % or more, and can contain 10 wt % or more, 15 wt % or more, 20 wt % or more, 25 wt % or more, 30 wt % or more, 35 wt % or more, 40 wt % or more, 45 wt % or more, 50 wt % or more, 55 wt % or more, 60 wt % or more, 65 wt % or more, 70 wt % or more, 75 wt % or more, 80 wt % or more, 85 wt % or more, even 89 or 90 wt % or more while at the same time typically comprises 90 wt % or less, 89 wt % or less, 85 wt % or less, 80 wt % or less, 75 wt % or less, 70 wt % or less, 65 wt % or less, 60 wt % or less, 55 wt % or less, 50 wt % or less, 45 wt % or less, 40 wt % or less, 35 wt % or less, 30 wt % or less, 25 wt % or less, 20 wt % or less, 15 wt % or less, 10 wt % or less, even 5 wt % or less polysaccharide component based on combined weight of polysaccharide, polysiloxane and additional crosslinking components.

The crosslinked polysiloxane elastomer can comprise crosslinking components other than the polysaccharide component. Additional crosslinking components establish crosslinks that are free of saccharide units between polysiloxane chains. Examples of suitable crosslinking components include remnants (that is, components left after the alkenyl groups of the crosslinker react with SiH groups on a polysiloxane to form a bond) of vinyl siloxanes, hexenyl siloxanes, allyl polyethers, methallyl polyethers, and di-terminal olefins (that is, olefins with carbon-carbon double bonds on two terminal ends). Additional crosslinking components can account for zero mol % or more, optionally 5 mol % or more, 10 mol % or more, 15 mol % or more, 20 mol % or more, 25 mol % or more, 30 mol % or more, 35 mol % or more, 40 mol % or more, 45 mol % or more, 50 mol % or more, 55 mol % or more, 60 mol % or more, 65 mol % or more, 70 mol % or more, 75 mol % or more, 80 mol % or more, even 85 mol % or more and at the same time typically 90 mol % or less, 85 mol % or less, 80 mol % or less, 75 mol % or less, 70 mol % or less, 65 mol % or less, 60 mol % or less, 55 mol % or less, 50 mol % or less, 45 mol % or less, 40 mol % or less, 35 mol % or less, 30 mol % or less, 25 mol % or less, 20 mol % or less, 15 mol % or less, 10 mol % or less, 5 mol % or less, 3 mol % or less, or even one mol % or less of the crosslinking bonds in the crosslinked polysiloxane elastomer.

The composition of the present invention can and typically does further comprise a solvent, sometimes called a carrier fluid, that swells the crosslinked polysiloxane elastomer so as to form a gel. A "gel" is a diluted cross-linked system that is homogeneous and exhibits no flow when in a steady state. "Homogeneous" means the combination does not phase separate from one another. "Exhibits no flow" means the combination does not flow when inverted in a vial as described in the Examples section, below. The crosslinked polysiloxane elastomer acts as a thickener for the solvent by increasing the viscosity of the solvent. The solvent can be, for example, any one or any combination of fluids selected from a group consisting of hydrocarbons, ethers, esters, alcohols, and siloxane fluids. Examples of suitable hydrocarbon fluids include farnesane, squalane, isohexadecane, undecane, tridecane and isododecane. Examples of suitable ether fluids include material sold under the name CETIOL™ OE from BASF (CETIOL is a trademark of Cognis IP Management GMBH), ethyl 3-(2,4-dimethyl-1,3-dioxolan-2-yl)propanoate, ethyl glycerin acetal levulinate, ethyl phenethyl acetal, and isopropylideneglyceryl cocoate. Examples of suitable ester fluids include isodecyl neopentanoate, isostearyl neopentanoate, isononyl isononanoate, ethyl acetate, capric triglyceride, caprylic triglyceride, triheptanoin, triisostearin, diisopropyl acetate, diisopropyl adipate, diisobutyl adipate, diethylhexyl adipate, n-propyl acetate, isobutyl acetate, n-butyl acetate, trimethylolpropane tricaprylate, trimethylolpropane tricaprate, dipentaerythrityl hexa C5-9 acid esters, C12-15 alkyl benzoate, triethylhexanoin, neopentyl glycol diheptanoate, diheptylsuccinate, heptylundecylenate, propylene glycol dibenzoate, dipropylene glycol dibenzoate, ethylhexyl palmitate, ethylhexyl stearate, isopropyl laurate, hexyl laurate, isopropyl myristate, isopropyl palmitate, n-butyl stearate, propylene glycol dicaprylate, propylene glycol dicaprate, coco caprylate, coco caprate, ethylhexyl cocoate, oleyl erucate, propylhelptyl caprylate, decyl oleate, hexyldecyl stearate, and propylene glycol laurate. Examples of suitable siloxane fluids include cyclic siloxanes such as cyclotetrasiloxane such as that available as DOWSIL™ 244 Fluid (DOWSIL is a trademark of The Dow Chemical Company), cyclopentasiloxane such as that available as DOWSIL™ 245 Fluid, or cyclohexasiloxane such as that available as DOWSIL™ 246 Fluid, linear and branched alkyl and aryl siloxanes such as caprylyl methicone such as that available as DOWSIL™ FZ-3196, and linear dimethylsiloxanes such as that available as DOWSIL™ 200 Fluids, and phenyl trimethicone such as that available as DOWSIL™ 556 Fluid.

The solvent can be a "high volatility" solvent selected from isododecane (boiling point of 210° C. at 101 MegaPascals pressure), farnesane (boiling point of 252° C. at 101 MegaPascals pressure), undecane (boiling point of 195° C. at 101 MegaPascals pressure), n-dodecane (boiling point of 216° C. at 101 MegaPascals pressure) and tridecane (boiling point of 234° C. at 101 MegaPascals pressure). These solvents form gels that can be turned into pastes having greater wash durability than pastes made from typical purely silicone elastomers.

The concentration of solvent in the gelled crosslinked polysiloxane elastomer composition is desirably 25 wt % or more, preferably 30 wt % or more, 35 wt % or more, 40 wt % or more, 45 wt % or more, 50 wt % or more, 55 wt % or more, 60 wt % or more, 65 wt % or more 70 wt % or more, 75 wt % or more, even 80 wt % or more while at the same time is typically 85 wt % or less, 80 wt % or less, 75 wt % or less, 70 wt % or less, 65 wt % or less, 60 wt % or less, 55 wt % or less, 50 wt % or less, 45 wt % or less, 40 wt % or less, 35 wt % or less based on combined weight of solvent and crosslinked polysiloxane elastomer.

The gel of solvent and crosslinked polysiloxane elastomer is desirably translucent or transparent to visible light, but it can be opaque.

The gel of solvent and crosslinked polysiloxane elastomer can further include additional components, particularly those useful in cosmetic applications. For instance, the gel can comprise any one or combination of more than one component selected from emollients, waxes, moisturizers, vegetable oils, synthetic oils, petrolatum, botanical extracts, vitamins, proteins, amino acids and their derivatives, fillers, ultraviolet light absorbers, sunscreens, anti-dandruff agents, antiperspirant agents, deodorant agents, skin protectants, hair dyes, fragrances, essential oils, pigments and colorants, and/or other actives or additives useful in cosmetics. The additional components can be added before, during or after the hydrosilylation reaction creating the gel.

The gel of solvent and crosslinked polysiloxane elastomer demonstrates desirable properties for cosmetic applications. In particular, the gel demonstrates desirable sensory properties, durability, and solvent compatibility. The methods for determining and evaluating these properties are set forth below in the Examples section. As a result, crosslinked polysiloxane elastomers and especially gels of solvent and crosslinked polysiloxane elastomers of the present invention are useful and desirable in cosmetic applications that are in the form of, for example: creams, aqueous solutions, emulsions (water-in-oil or oil-in-water), oils, ointments, pasts, gels, lotions, milks, foams, sticks and suspensions. The cosmetic can be for personal care applications such as color cosmetics, facial and body care cosmetics, leave-on hair care, and topical care products.

It is desirable to prepare the crosslinked polysiloxane elastomer of the present invention using a hydrosilylation reaction between reactants comprising an SiH functional polysiloxane and an alkenyl-functional, preferably vinyl functional, polysaccharide, and optionally additional crosslinking additives. The SiH functional polysiloxane can be linear or branched. The SiH functional polysiloxane comprises two or more SiH functionalities per molecule. The SiH content of the polysiloxane is preferably 0.02 wt % or more, 0.05 wt % or more, 0.08 wt % or more, 0.10 wt % or more, 0.15 wt % or more, 0.20 wt % or more, 0.25 wt % or more, 0.30 wt % or more, 0.35 wt % or more, 0.40 wt % or more, 0.45 wt % or more, 0.50 wt % or more, 0.55 wt % or more, 0.60 wt % or more, 0.65 wt % or more, 0.70 wt % or more, 0.75 wt % or more, 0.85 wt % or more, 0.90 wt % or more, even 0.95 wt % or more while at the same time is typically 1.5 wt % or less, 1.25 wt % or less, 1.0 wt % or less, and can be 0.9 wt % or less, 0.8 wt % or less, 0.6 wt % or less, 0.5 wt % or less, 0.4 wt % or less, even 0.3 wt % or less, or 0.2 wt % or less based on polysiloxane weight. Wt % SiH refers to mass of silicon-bound hydrogen divided by mass of the polymer times 100%. Determine SiH content by infrared spectroscopy according to the method of CN103674889A.

The SiH functional polysiloxane can comprise any combination of M-type, D-type, T-type and Q-type siloxane units. Desirably, the SiH functional polysiloxane is linear comprising M-type and D-type polysiloxane units and has a degree of polymerization of zero or more, one or more, 2 or more, 3 or more, 4 or more, 5 or more, 6 or more, 7 or more, 8 or more, 9 or more, 10 or more, 15 or more, 20 or more, 30 or more, 40 or more, 50 or more, 75 or more, 100 or more, even 150 or more and most desirably 200 or less, and can be 150 or less, 100 or less, 75 or less, 50 or less, 40 or less, 30 or less, 20 or less, even 10 or less where degree of polymerization is the number of D-type units in the polysiloxane. If the linear polysiloxane exceeds a DP of 200 the resulting crosslinked polysiloxane elastomer tends to be weak and pliable as a gel. Most desirably, the DP is 20 or less, preferably 15 or less or even lower in order to maximize the concentration of biorenewable polysaccharide component in the crosslinked polysiloxane elastomer.

The polysaccharide component is desirably a silylated polysaccharide that comprises linked fructose, galactose, anhydrogalactose, or glucose saccharide units provided that glycosidic linkages of glucose are alpha linkages and that the silylated polysaccharide is other than a silylated starch; and is further characterized by having on average one mole-percent (mol %) or more, preferably 5 mol % or more, 10 mol % or more, 15 mol % or more, 20 mol % or more, 30 mol % or more, 33 mole-percent (mol %) or more, preferably 35 mol % or more, 37 mol % or more, 40 mol % or more, 50 mol % or more, 60 mol % or more, 70 mol % or more, 80 mol % or more, even 90 mol % or more while at the same time 100 mol % or less of the hydroxyl groups on the polysaccharide silylated with a silyl group having the structure —$SiR_3$ linked to the polysaccharide through a C—O—Si bond where each R is independently selected from hydrocarbyl radicals having from one to 12 carbon atoms, provided that on average at least 2.0 R groups per polysaccharide have a terminally unsaturated carbon-carbon double bond (for example, vinyl groups). Frequently, the R components of the —$SiR_3$ group are selected from methyl and vinyl groups. Desirably, the silylated polysaccharide is selected from a group consisting of silylated alpha-cyclodextrin, silylated beta-cyclodextrin, silylated gamma-cyclodextrin, silylated maltodextrin, silylated pullulan, silylated dextran, silylated trehalose, silylated inulin, and silylated agarose. The silylated polysaccharide desirably contains 2 to 2000 saccharide units per molecule, with optional limits on number of saccharide units bonded together as taught herein above for the polysaccharide component of the elastomer.

The amount of SiH functional polysiloxane and alkenyl-functional polysaccharide is desirably such that the molar ratio of SiH groups to alkenyl groups in the polysaccharide is greater than 0.7, preferably 0.8 or more, 0.9 or more, 1.0 or more, 1.1 or more, 1.2 or more, 1.3 or more, even 1.4 or more while at the same time is typically 1.5 or less, preferably 1.4 or less, 1.2 or less, 1.1 or less, or even 1.0 or less. Determine the ratio of SiH to alkenyl from the molar ratio of the components used in the reaction and the average molar amount of each functional group on the components used. The molar concentration of SiH can be determined from the supplier of the SiH functional polysiloxane or, if not available from the supplier then by infrared spectroscopy according to the method of CN103674889A. The molar concentration of alkenyl groups can be determined from the components used to make the alkenyl-functional polysaccharide and/or $^1$H NMR analysis of the alkenyl-functional polysaccharide.

The hydrosilylation reaction further requires a platinum-based hydrosilylation catalyst. Platinum-based hydrosilylation catalysts include compounds and complexes such as platinum (0)-1,3-divinyl-1,1,3,3-tetramethyldisiloxane (Karstedt's catalyst), $H_2PtCl_6$, di-.μ.-carbonyl di-.π.-cyclopentadienyldinickel, platinum-carbonyl complexes, platinum-divinyltetramethyldisiloxane complexes, platinum cyclovinylmethylsiloxane complexes, platinum acetylacetonate (acac), platinum black, platinum compounds such as chloroplatinic acid, chloroplatinic acid hexahydrate, a reaction product of chloroplatinic acid and a monohydric alcohol, platinum bis(ethylacetoacetate), platinum bis(acetylacetonate), platinum dichloride, and complexes of the platinum compounds with olefins or low molecular weight organopolysiloxanes or platinum compounds microencapsulated in a matrix or core-shell type structure. The hydrosilylation catalyst can be part of a solution that includes complexes of platinum with low molecular weight organopolysiloxanes that include 1,3-diethenyl-1,1,3,3-tetramethyldisiloxane complexes with platinum. These complexes may be microencapsulated in a resin matrix. The catalyst can be 1,3-diethenyl-1,1,3,3-tetramethyldisiloxane complex with platinum. The concentration of platinum-based hydrosilylation catalyst in the hydrosilylation is typically 5 weight-parts per million (ppm) or more, preferably 10 ppm or more, and can be 25 ppm or more, 50 ppm or more, even 75 ppm or more while at the same time is typically 500 ppm or less, 400 ppm or less, 300 ppm or less, 200 ppm or less and preferably 100 ppm or less and can be 90 ppm or less, 80 ppm or less, 70 ppm or less, 60 ppm or less, even 50 ppm or less based on weight of polysaccharide component, polysiloxane component, solvent and any additional crosslinker.

The hydrosilylation reaction to form the elastomer can further include additional crosslinking additives. The additional crosslinking additives comprise multiple alkenyl functionalities per molecule and serve as crosslinking components in addition to the alkenyl-functional polysaccharide. Additional crosslinking additives are not required, but can be present to supplement crosslinking. Examples of suitable additional crosslinking additives include vinyl terminated polydimethylsiloxane, poly(dimethyl, methylvinyl)siloxane, vinyl terminated poly(dimethyl, methylvinyl)siloxane, hexenyl terminated polydimethylsiloxane, 1,5-hexadiene, 1,11-dodecadiene, 1,15-hexadecadiene, bis(methallyl)poly(ethylene oxide), bis(allyl)poly(ethylene oxide), bis(methallyl) poly(propylene oxide), and bis(allyl)poly(propylene oxide).

If present, the additional crosslinking additives are present at a concentration that provides zero mol % or more, optionally 5 mol % or more, 10 mol % or more, 15 mol % or more, 20 mol % or more, 25 mol % or more, 30 mol % or more, 35 mol % or more, 40 mol % or more, 45 mol % or more, 50 mol % or more, 55 mol % or more, 60 mol % or more, 65 mol % or more, 70 mol % or more, 75 mol % or more, 80 mol % or more, even 85 mol % or more and at the same time typically 90 mol % or less, 85 mol % or less, 80 mol % or less, 75 mol % or less, 70 mol % or less, 65 mol % or less, 60 mol % or less, 55 mol % or less, 50 mol % or less, 45 mol % or less, 40 mol % or less, 35 mol % or less, 30 mol % or less, 25 mol % or less, 20 mol % or less, 15 mol % or less, 10 mol % or less, 5 mol % or less, 3 mol % or less, or even one mol % or less of the alkenyl groups relative to combined moles of alkenyl groups provided by the alkenyl-functional polysaccharide and the additional crosslinking additive(s).

The reaction is typically conducted in a solvent compatible with both the polysiloxane and the resulting silylated polysaccharide, and that becomes a carrier fluid that swells the elastomer into a gel as the elastomer is made. The solvent can be, for example, selected from a group consisting of hydrocarbons, ethers, esters, alcohols and siloxane fluids as taught previously above for the solvent included in the gelled crosslinked polysiloxane elastomer. The concentration of solvent in the reaction mixture is typically 25 wt % or more, preferably 30 wt % or more, 35 wt % or more, 40 wt % or more, 45 wt % or more, 50 wt % or more, 55 wt % or more, 60 wt % or more, 65 wt % or more 70 wt % or more, 75 wt % or more, even 80 wt % or more while at the same time is typically 85 wt % or less, 80 wt % or less, 75 wt % or less, 70 wt % or less, 65 wt % or less, 60 wt % or less, 55 wt % or less, 50 wt % or less, 45 wt % or less, 40 wt % or less, 35 wt % or less based on combined weight of solvent, SiH functional polysiloxane, alkenyl-functional polysaccharide and any additional crosslinking additives.

Carry out the hydrosilylation reaction by combining the solvent, SiH functional polysiloxane, alkenyl-functional polysaccharide, any additional crosslinkers and platinum-based catalyst together and stir them to form a reaction mixture, generally at 25° C. Heat the reaction mixture generally to a temperature in a range of 70-90° C. while stirring. Continue stirring until a gel forms and stirring ceases. Heat the gel for a period of time to complete the reaction, typically by placing the gel in an oven at 70° C. for 3 hours. Specific examples of hydrosilylation reactions to prepare the crosslinked polysiloxane elastomer of the present invention are in the Examples section, below. The hydrosilylation reaction results in a crosslinked polysiloxane elastomer gel that comprises the crosslinked polysiloxane elastomer of the present invention swollen to form a gel with the solvent used in the hydrosilylation reaction. The hydrosilylation reaction prepares the crosslinked polysiloxane elastomer of the present invention as well as the crosslinked polysiloxane elastomer gel of the present invention. The crosslinked polysiloxane elastomer gel can be transparent, or translucent, or opaque relative to visible light, but is desirably transparent.

The hydrosilylation reaction can be run in the absence of unsaturated organic molecules other than the silylated polysaccharide and/or unsaturated siloxanes.

The crosslinked polysiloxane gel can be mixed under shear with or without additional solvent and/or post cure quenching agents to form a paste. Suitable post cure quenching agents include any one or any combination of more than one selected from a group consisting of vinyl-t-butyldimethylsilane, vinyldiethylmethylsilane, vinylethyldimethylsilane, vinyltriethylsilane, vinyltrimethylsilane, divinyldimethylsilane, divinyltetramethyldisilane, vinylpentamethyldisiloxane, 1,3-divinyltetramethyldisiloxane, tetrakis(dimethylvinylsilyl) silicate, vinylsilanes, terminal linear vinyl siloxanes, pendant linear vinyl siloxanes, terminal branched vinyl siloxanes, pendant branched vinyl siloxanes, pendant and terminal branched siloxanes, and cyclic vinyl siloxanes. The resulting paste can be translucent or transparent to visible light, homogeneous, stable to phase separation, and has desirable sensory properties as described in the Examples section, below.

Examples

Table 1 lists the component used to prepare alkenyl-functional polysaccharides used to make the crosslinked polysiloxane elastomers described in the next section.

TABLE 1

| Component | Description | Source |
|---|---|---|
| Solvent | N,N-Dimethylacetamide | Sigma-Aldrich |
| Polysaccharide 1 | Beta-cyclodextrin | Oakwood Chemical (cat # 097691) |
| Polysaccharide 2a | Maltodextrin, Dextrose equivalent 6.5 | Grain Processing Corporation (MALTRIN ™ 040) |
| Polysaccharide 2b | Maltodextrin, Dextrose equivalent 24.1 | Grain Processing Corporation (MALTRIN ™ 250) |
| Polysaccharide 3 | Dextran (150,000 Daltons) | Sigma-Aldrich |
| Polysaccharide 4 | Inulin | Sigma-Aldrich (catalog #12255) |
| Polysaccharide 5 | Pullulan | TCI (catalog #P0978) |
| Polysaccharide 6 | Trehalose Dihydrate | Sigma-Aldrich (catalog #T5251) |
| Polysaccharide 7 | Methyl beta-cyclodextrin | Alfa Aesar (catalog #J66847) |
| Silazane 1 | Hexamethyldisilazane | Sigma-Aldrich |
| Silazane 2 | 1,1,3,3-tetramethyl-1,3-divinyldisilazane | Gelest (catalog #SID4612.0) |
| Catalyst 1 | Saccharin | Sigma-Aldrich |

MALTRIN is a trademark of Grain Processing Corporation

Preparation of Alkenyl-Functional Polysaccharides

Prepare the samples in the following manner using the formulation in Table 2. For those samples indicating the polysaccharide was dried, dry the polysaccharide prior to the reaction in vacuum (1.3 kilopascals, 10 mm Hg) at 90 degrees Celsius (° C.) for 24 hours. Add the specified amount of polysaccharide, silazane, catalyst and solvent to a 40-milliliter vial. Add a polytetrafluoroethylene stir bar and inert the vial by purging with nitrogen gas and sealing with a septum. Place the vial on a heating block and heat to the stated temperature for the stated period while stirring. Then allow the sample to cool and dry under vacuum (1.3 kilopascals, 10 mm Hg) for 24 hours to yield the silylated polysaccharide sample.

Determine extent of hydroxyl silylation and extent of alkenyl substitution by proton nuclear magnetic resonance spectroscopy ($^1$H NMR). For example, dissolve a 10-milligram sample in 0.6 milliliters of d6-benzene and analyze by $^1$H NMR in a 400 MHz Varian NMR spectrometer. Use a 5 second acquisition time and a relaxation delay time of 15 seconds and collect 16 scans. Reference final spectra to residual benzene at δ 7.16 ppm. Regions for the particular groups in the spectra are: unsaturated region ("U") integrated over δ 5.6-6.5 ppm to account for either: all 3 protons of vinyl groups ("U"="A") or 1 proton of other terminal alkenyl groups (3"U"="A"), saccharide region ("S") is integrated over δ 3.6-4.6 ppm, and methyl region ("M") is integrated over δ 0.20-0.55 ppm. Normalize the saccharide region to methanediyl and methanetriyl hydrogens excluding the anomeric carbon hydrogen.

Determine the following sample attributes according to their associated calculations:

Mole-percent (%) —OH substitution=[(A/3)+(M−2*A)]/[—OH per starting saccharide]*100=the mol % of hydroxyl groups on the polysaccharide that have been silylated with —$SiR_3$ linked to the polysaccharide through a C—O—Si bond.

Mole-percent terminal alkenyl substitution (% Alkenyl)=[(A/3)]/[(A/3)±(M−2*A)]*100%

Terminal Alkenyl groups per polysaccharide=[(% Alkenyl)]*[mol % —OH substitution]*[—OH per starting saccharide]*[Degree of Polymerization]/$10^4$ where:

"[Mol % —OH per starting saccharide]" is 2 for agarose, 4 for disaccharides and 3 for all other polysaccharides in scope of the present invention.

"Degree of Polymerization" refers to the number of polysaccharide units per polysaccharide molecule and can be obtained from the supplier of the polysaccharide or by determined using routine GPC methods.

For samples in the Experimental section that are insoluble in d6-benzene, determine mole-percent hydroxyl substitution by neutron activation analysis (NAA). Prepare duplicate analyte materials by transferring 1.0 grams of sample into pre-cleaned 2-dram polyethylene vials. Prepare silicon standard aliquots from NIST traceable standard solutions by taking appropriate amounts into similar vials to the samples. Dilute to the same volumes as the analyte materials using pure water. Also prepare a blank containing only pure water. Analyze the analyte materials, standards and blank following standard NAA procedure—irradiating for 2 minutes at 100 kW. After a waiting time of 9 minutes, carry out gamma ray spectroscopy using high purity germanium detectors. Determine silicon concentrations (wt % Si) using standard comparative technique with CANBERRA software. Calculate the mol % —OH substitution using the following calculations:

Mol % —OH substitution=([MW of starting polysaccharide repeat unit]*[wt % Si])/{(28−84*[wt % Si]/100)*[—OH per starting saccharide]}.

This value corresponds to the mol % of hydroxyl groups on the polysaccharide that have been silylated with and —$SiR_3$ linked to the polysaccharide through a C—O—Si bond.

where:

[MW of repeating polysaccharide repeat unit] is 154 for agarose, 171 for disaccharides and 162 for all other polysaccharides in scope of the present invention.

[—OH per starting saccharide] is 2 for agarose, 4 for disaccharides and 3 for all other polysaccharides.

Table 2 presents formulations for the silylated polysaccharide samples. The amount of polysaccharide is provided in grams (g). The amount of catalyst and amount of silazane are each presented in moles per mole of saccharide units in the specified grams of polysaccharide ("equiv"). The solvent concentration is present in molar concentration of the specified amount of polysaccharide in the combined volume of solvent and silazane ("M"). "DP" refers to degree of polymerization for the polysaccharides, which is the number of saccharide units bound together in the polysaccharide.

TABLE 2

| Alkenyl-Functional Polysac-charide | Polysac-charide (g) | DP | Catalyst (equiv) | Solvent (M) | Silazane (equiv) | Temp (° C.) | Time (hours) | Mol % OH Substitution | Mol % vinyl | Wt % Vinyl | Vinyl Functionality per Polysac-charide |
|---|---|---|---|---|---|---|---|---|---|---|---|
| 1 | 1 (1.0) | 7 | None | 1 (0.6) | 2 (4) | 110 | 18 | 77 | 100 | 17.49 | 16 |
| 2 | 1 (1.0) | 7 | None | 1 (0.75) | 2 (2.5) | 110 | 8 | 37 | 100 | 8.67 | 7.7 |
| 3 | 1* (50.0) | 7 | 1 (0.003) | 1 (2.5) | 1 (1.35) + 2 (0.15) | 110 | 3 | 77 | 10 | 1.98 | 1.6 |
| 4 | 1* (50.0) | 7 | 1 (0.006) | 1 (2.1) | 1 (1.25) + 2 (0.25) | 110 | 3 | 77 | 15 | 2.87 | 2.4 |
| 5 | 1* (50.0) | 7 | 1 (0.003) | 1 (2.5) | 1 (1.15) + 2 (0.35) | 110 | 3 | 73 | 23 | 4.27 | 3.5 |
| 6 | 1* (50.0) | 7 | 1 (0.005) | 1 (2.4) | 1 (1.0) + 2 (0.5) | 110 | 2 | 70 | 33 | 5.66 | 4.9 |
| 7 | 2b (10.0) | 4.5 | 1 (0.003) | 1 (1.8) | 1 (1.48) + 2 (0.63) | 70 | 15 | 77 | 40 | 7.3 | 4.1 |
| 8 | 2a* (1.0) | 17 | 1 (0.003) | 1 (1.7) | 2 (2) | 70 | 6 | 100 | 100 | 19.57 | 51 |
| 9 | 2a* (1.0) | 17 | 1 (0.003) | 1 (1.8) | 1 (1.45) + 2 (0.05) | 70 | 5 | 80 | 8 | 1.54 | 3.3 |
| 10 | 2b* (1.0) | 4.5 | 1 (0.003) | 1 (2.1) | 1 (1.25) + 2 (0.25) | 110 | 1 | 90 | 21 | 4.2 | 2.6 |
| 11 | 2b* (1.0) | 4.5 | 1 (0.003) | 1 (1.8) | 2 (1.5) | 70 | 5 | 80 | 100 | 17.8 | 10.8 |
| 12 | 5* (1.0) | 1850 | 1 (0.003) | 1 (1.8) | 2 (1.5) | 70 | 3 | 80 | 100 | 17.8 | 4440 |
| 13 | 5* (1.0) | 1850 | 1 (0.003) | 1 (2.1) | 1 (1.47) + 2 (0.03) | 110 | 3 | 80 | 3 | 0.58 | 133 |
| 14 | 3* (1.0) | 925 | 1 (0.003) | 1 (2.1) | 2 (1.5) | 110 | 6 | 83 | 100 | 0.76 | 2315 |
| 15 | 3* (1.0) | 925 | 1 (0.003) | 1 (2.1) | 1 (1.46) + 2 (0.04) | 70 | 2.5 | 77 | 4 | 18.2 | 85 |
| 16 | 6 (1.0) | 2 | 1 (0.005) | 1 (2.1) | 2 (1.5) | 110 | 4 | 90 | 100 | 6.52 | 7.2 |
| 17 | 6 (1.0) | 2 | 1 (0.001) | 1 (0.6) | 1 (4.84) + 2 (1.86) | 70 | 1 | 50 | 52 | 20.6 | 2.1 |
| 18 | 4* (1.0) | 18 | 1 (0.003) | 1 (2.1) | 1 (1.39) + 2 (0.11) | 110 | 1 | 67 | 8 | 1.4 | 2.9 |
| 19 | 4* (1.0) | 18 | 1 (0.003) | 1 (2.1) | 2 (1.5) | 70 | 2 | 37 | 100 | 11.7 | 19.8 |
| 20 | 1* (1.0) | 7 | None | 1 (0.6) | 1 (4.0) | 110 | 24 | 80 | 0 | 0 | 0 |
| 21 | 1* (1.0) | 7 | 1 (0.003) | None (2.4) | 2 (2) | 70 | 6 | 75 | 100 | 17.3 | 15.8 |
| 22 | 2b (20) | 4.5 | 1 (0.005) | 1 (1.8) | 1 (1.47) + 2 (0.63 | 70 | 4 | 84 | 37 | 7.1 | 4.8 |
| 23 | 7 (1.0) | 7 | 1 (0.003) | 1 (4.3) | 1 (1.0) | 110 | 4 | 100 | 0 | 0 | 0 |

*dried prior to use.

Preparation of Crosslinked Polysiloxane Elastomers

Table 3 lists the materials for use in addition to the alkenyl-functional polysaccharides in Table 2 for making the crosslinked polysiloxane elastomers of the samples described below.

TABLE 3

| Component | Description | Source |
|---|---|---|
| Platinum-based catalyst | 1,3-diethenyl-1,1,3,3-tetramethyldisiloxane platinum complex | Available under the name SYL-OFF ™ 4000 Catalyst from The Dow Chemical Company. |
| Additional Crosslinker 1 | Vinyl terminated polydimethylsiloxane (4-8 centistoke): 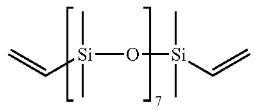 | Available as DMS-V05 from Gelest. |
| Additional Crosslinker 2 | Hexenyl Terminated polydimethylsiloxane, where n = 100: 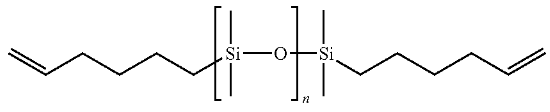 | Prepare according to US20200010734A1 |
| Additional Crosslinker 3 | 1,5-hexadiene | Sigma-Aldrich |
| Additional Crosslinker 4 | Bis(methylallyl)poly(ethylene oxide)EO14, 7.28 wt % alkene: 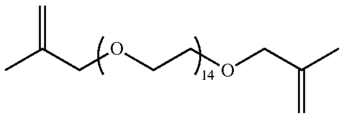 | DMUS-5 from NOF Corporation. |
| Additional Crosslinker 5 | Bis(allyl)poly(ethylene oxide)$EO_{25}$ with 4.28 wt % alkene: | DUS-80 from NOF Corporation |

TABLE 3-continued

| Component | Description | Source |
|---|---|---|
| | 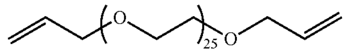 | |
| SiH-Functional Polysiloxane 1 | H—$[(CH_3)_2SiO]_n$—$(CH_3)_2Si$—H; where n = 6.5 | Synthesize according to U.S. Pat. No. 4,370,358 (see columns 4-5). |
| SiH-Functional Polysiloxane 2 | H—$[(CH_3)_2SiO]_n$—$(CH_3)_2Si$—H; where n = 16.5 | Synthesize according to U.S. Pat. No. 4,370,358 (see solumn 4-5). |
| SiH-Functional Polysiloxane 3 | H—$[(CH_3)_2SiO]_n$—$(CH_3)_2Si$—H; where n = 38 | Synthesize according to U.S. Pat. No. 4,370,358 (see solumn 4-5). |
| SiH-Functional Polysiloxane 4 | H—$[(CH_3)_2SiO]_n$—$(CH_3)_2Si$—H; where n = 100 | Synthesize according to U.S. Pat. No. 4,370,358 (see columns 4-5). |
| SiH-Functional Polysiloxane 5 | $CH_3$—$[(CH_3)HSiO]_x$—$[(CH_3)_2SiO]_y$—$(CH_3)_2Si$ Where x = 6 and y = 92 | Synthesize according to US2823218 (see column 3) |
| SiH-Functional Polysiloxane 6 | $CH_3$—$[(CH_3)HSiO]_x$—$[(CH_3)_2SiO]_y$—$(CH_3)_2Si$ Where x = 55 and y = 33 | Synthesize according to US2823218 (see column 3) |
| SiH-Functional Polysiloxane 7 | $[H(CH_3)_2SiO]_3SiO$—$[H(CH_3)_2SiO]_2SiO$—$(CH_3O)(HO)SiO$—$Si[OSiH(CH_3)_2]_3$ | Synthesize according to U.S. Pat. No. 5,310,843 (see column 4). |
| Solvent 1 | Isododecane | Lanxess |
| Solvent 2 | Farnesane | Available as NEOSSANCE ™ Hemisqualane from Aprinnova |
| Solvent 3 | Dioctyl Ether | Available under the name CETIOL ™ OE from BASF |
| Solvent 4 | Isodecyl neopentanoate | Available as CERAPHYL ™ SLK Ester from AShland |
| Solvent 5 | Decamethylcyclopentasiloxane | Available as XIAMETER ™ PMX-0245 Fluid from The Dow Chemical Company. |

SYL-OFF and XIAMETER are trademarks of Dow Corning Corporation.
CETIOL is a trademark of Cognis IP Management GMBH.
CERAPHYL is a trademark of ISP investments LLC.
NEOSSANCE is a trademark of Amyris, Inc.

Prepare the crosslinked polysiloxane elastomers by hydrosilylation with the formulations set forth in Table 4, where amounts of components are in grams (g). Use the following reaction procedure. Add the specified amount of vinyl-functionalized polysaccharide and solvent to a 20-milliliter scintillation vial equipped with a magnetic stir bar. Begin stirring and heat the contents to 70° C. for 15 minutes to dissolve components to a homogeneous solution. Add the specified amount of SiH functional polysiloxane and any additional crosslinker. Heat the reaction mixture at 70° C. for 10 minutes and then add the platinum-based catalyst. Heat for another 3 hours at 70° C. Allow to cool to 25° C. Successful reactions (that is, successful cures) are evident by formation of a gel that did not flow more than 1 centimeter in the scintillation vial when inverting for one minute.

Table 4 identifies the components used and concentration of the components used (in parentheses) in grams of the component used, except for the catalyst which is in weight parts Pt metal per million weight part of the entire mixture. Table 4 also presents the molar ratio of SiH functionality to vinyl functionality in the formulation, wt % of the reactants and whether the composition cured to an elastomer successfully or not.

TABLE 4

| Sample | Alkenyl-Functional Polysaccharide (g/wt % of reactants) | Alkenes per Polysaccharide | SiH-Functional Polysiloxane (g/wt % of reactants) | Additional Crosslinker (g/wt % of reactants) | Solvent (g/wt %) | Pt-Based Catalyst | SIH:Vi Molar ratio | Cured? |
|---|---|---|---|---|---|---|---|---|
| A | 4 (0.18 g/60 wt %) | 2.4 | 2 (0.12 g/40 wt %) | None | 2 (1.69 g/85 wt %) | 20 ppm | 0.90 | NO |
| 1 | 4 (0.21 g/62 wt %) | 2.4 | 2 (0.13 g/38 wt %) | None | 2 (1.65 g/82 wt %) | 20 ppm | 0.90 | Yes |
| 2 | 4 (0.36 g/60 wt %) | 2.4 | 2 (0.24 g/40 wt %) | None | 2 (1.39 g/70 wt %) | 20 ppm | 0.90 | Yes |
| 3 | 4 (0.39 g/39 wt %) | 2.4 | 2 (0.61 g/61 wt %) | None | 2 (1.00 g/50 wt %) | 20 ppm | 0.90 | Yes |
| B | 4 (0.85 g/61 wt %) | 2.4 | 2 (0.55 g/39 wt %) | None | 2 (0.59 g/30 wt %) | 20 ppm | 0.90 | NO |
| C | 4 (0.44 g/73 wt %) | 2.4 | 2 (0.16 g/27 wt %) | None | 2 (1.39 g/70 wt %) | 20 ppm | 0.50 | NO |
| 4 | 4 (0.36 g/60 wt %) | 2.4 | 2 (0.24 g/40 wt %) | None | 2 (1.39 g/70 wt %) | 20 ppm | 0.90 | Yes |
| 5 | 4 (0.33 g/55 wt %) | 2.4 | 2 (0.27 g/45 wt %) | None | 2 (1.39 g/70 wt %) | 20 ppm | 1.1 | Yes |
| D | 4 (0.29 g/48 wt %) | 2.4 | 2 (0.31 g/52 wt %) | None | 2 (1.39 g/70 wt %) | 20 ppm | 1.5 | NO |
| E | 3 (0.41 g/68 wt %) | 1.6 | 2 (0.19 g/32 wt %) | None | 2 (1.39 g/70 wt %) | 20 ppm | 0.90 | NO |
| 6 | 4 (0.36 g/60 wt %) | 2.4 | 2 (0.24 g/40 wt %) | None | 2 (1.40 g/70 wt %) | 10 ppm | 0.90 | Yes |
| 7 | 5 (0.31 g/52 wt %) | 3.5 | 2 (0.29 g/48 wt %) | None | 2 (1.39 g/70 wt %) | 20 ppm | 0.90 | Yes |
| 8 | 5 (0.31 g/52 wt %) | 3.5 | 2 (0.29 g/48 wt %) | None | 3 (1.39 g/70 wt %) | 20 ppm | 0.90 | Yes |
| 9 | 5 (0.31 g/52 wt %) | 3.5 | 2 (0.29 g/48 wt %) | None | 4 (1.39 g/70 wt %) | 20 ppm | 0.90 | Yes |
| 10 | 5 (0.31 g/52 wt %) | 3.5 | 2 (0.29 g/48 wt %) | None | 5 (1.39 g/70 wt %) | 20 ppm | 0.90 | Yes |
| 11 | 5 (0.31 g/52 wt %) | 3.5 | 2 (0.29 g/48 wt %) | None | 1 (1.39 g/70 wt %) | 20 ppm | 0.90 | Yes |
| 12 | 6 (0.26 g/43 wt %) | 4.9 | 2 (0.34 g/57 wt %) | None | 2 (1.39 g/70 wt %) | 20 ppm | 0.90 | Yes |
| 13 | 2 (0.20 g/33 wt %) | 7.7 | 2 (0.40 g/67 wt %) | None | 2 (1.39 g/70 wt %) | 100 ppm | 0.90 | Yes |
| 14 | 1 (0.12 g/20 wt %) | 16 | 2 (0.48 g/80 wt %) | None | 3 (1.39 g/70 wt %) | 100 ppm | 0.90 | Yes |
| 15 | 9 (0.44 g/73 wt %) | 3.3 | 2 (0.16 g/27 wt %) | None | 2 (1.39 g/70 wt %) | 100 ppm | 0.90 | Yes |

TABLE 4-continued

| Sample | Alkenyl-Functional Polysaccharide (g/wt % of reactants) | Alkenes per Polysaccharide | SiH-Functional Polysiloxane (g/wt % of reactants) | Additional Crosslinker (g/wt % of reactants) | Solvent (g/wt %) | Pt-Based Catalyst | SIH:Vi Molar ratio | Cured? |
|---|---|---|---|---|---|---|---|---|
| 16 | 8 (0.11 g/18 wt %) | 51 | 2 (0.49 g/82 wt %) | None | 2 (1.39 g/70 wt %) | 40 ppm | 0.90 | Yes |
| 17 | 10 (0.31 g/52 wt %) | 2.6 | 2 (0.29 g/48 wt %) | None | 2 (1.39 g/70 wt %) | 40 ppm | 0.90 | Yes |
| 18 | 11 (0.12 g/20 wt %) | 10.8 | 2 (0.48 g/80 wt %) | None | 2 (1.38 g/70 wt %) | 40 ppm | 0.90 | Yes |
| 19 | 16 (0.19 g/28 wt %) | 7.2 | 5 (0.43 g/72 wt %) | None | 2 (1.39 g/70 wt %) | 100 ppm | 0.90 | Yes |
| 20 | 17 (0.11 g/18 wt %) | 2.1 | 2 (0.49 g/82 wt %) | None | 2 (1.39 g/70 wt %) | 20 ppm | 0.90 | Yes |
| 21 | 18 (0.46 g/77 wt %) | 2.9 | 2 (0.14 g/23 wt %) | None | 2 (1.36 g/70 wt %) | 100 ppm | 0.90 | Yes |
| 22 | 18 (0.39 g/65 wt %) | 2.9 | 5 (0.21 g/35 wt %) | None | 2 (1.36 g/70 wt %) | 100 ppm | 0.90 | Yes |
| 23 | 19 (0.16 g/27 wt %) | 19.8 | 2 (0.44 g/73 wt %) | None | 4 (1.39 g/70 wt %) | 100 ppm | 0.90 | Yes |
| 24 | 13 (0.80 g/89 wt %) | 133 | 2 (0.10 g/11 wt %) | None | 3 (2.04 g/70 wt %) | 100 ppm | 0.90 | Yes |
| 25 | 12 (0.18 g/20 wt %) | 4440 | 2 (0.72 g/80 wt %) | None | 3 (2.04 g/70 wt %) | 100 ppm | 0.90 | Yes |
| 26 | 14 (0.77 g/86 wt %) | 2315 | 2 (0.13 g/14 wt %) | None | 2 (2.09 g/70 wt %) | 20 ppm | 0.90 | Yes |
| 27 | 15 (0.18 g/20 wt %) | 85 | 2 (0.72 g/80 wt %) | None | 2 (2.09 g/70 wt %) | 20 ppm | 0.90 | Yes |
| 28 | 4 (0.70 g/78 wt %) | 2.4 | 1 (0.20 g/22 wt %) | None | 2 (2.09 g/70 wt %) | 20 ppm | 0.90 | Yes |
| 29 | 5 (0.63 g/70 wt %) | 3.5 | 1 (0.27 g/30 wt %) | None | 2 (2.09 g/70 wt %) | 20 ppm | 0.90 | Yes |
| F | 3 (0.50 g/70 wt %) | 1.6 | 1 (0.10 g/48 wt %) | None | 2 (1.39/70 wt %) | 100 ppm | 0.90 | NO |
| 30 | 5 (0.46 g/51 wt %) | 3.5 | 2 (0.44 g/49 wt %) | None | 2 (2.09 g/70 wt %) | 20 ppm | 0.90 | Yes |
| 31 | 5 (0.28 g/31 wt %) | 3.5 | 3 (0.62 g/69 wt %) | None | 2 (2.09 g/70 wt %) | 20 ppm | 0.90 | Yes |
| 32 | 4 (0.36 g/40 wt %) | 2.4 | 3 (0.54 g/60 wt %) | None | 2 (2.09 g/70 wt %) | 20 ppm | 0.90 | Yes |
| G | 3 (0.29 g/83 wt %) | 1.6 | 3 (0.31 g/17 wt %) | None | 2 (1.39/70 wt %) | 20 ppm | 0.90 | NO |
| 33 | 4 (0.20 g/22 wt %) | 2.4 | 4 (0.70 g/78 wt %) | None | 2 (2.09 g/70 wt %) | 20 ppm | 0.90 | Yes |
| 34 | 5 (0.14 g/15 wt %) | 3.5 | 4 (0.76 g/85 wt %) | None | 2 (2.09 g/70 wt %) | 20 ppm | 0.90 | Yes |
| 35 | 5 (0.33 g/37 wt %) | 3.5 | 5 (0.57 g/63 wt %) | None | 2 (2.09 g/70 wt %) | 20 ppm | 0.90 | Yes |
| H | 3 (0.34 g/57 wt %) | 1.6 | 5 (0.26 g/43 wt %) | None | 2 (1.39 g/70 wt %) | 20 ppm | 0.90 | NO |
| 36 | 4 (0.81 g/89 wt %) | 2.4 | 6 (0.10 g/11 wt %) | None | 2 (2.09 g/70 wt %) | 20 ppm | 0.90 | Yes |
| 37 | 5 (0.78 g/87 wt %) | 3.5 | 6 (0.12 g/13 wt %) | None | 2 (2.09 g/70 wt %) | 20 ppm | 0.90 | Yes |
| 38 | 5 (1.05 g/88 wt %) | 3.5 | 7 (0.15 g/12 wt %) | None | 2 (2.8 g/70 wt %) | 20 ppm | 0.90 | Yes |
| 39 | 6 (1.01 g/84 wt %) | 4.9 | 7 (0.19 g/16 wt %) | None | 2 (2.8 g/70 wt %) | 20 ppm | 0.90 | Yes |
| 40 | 5 (0.27 g/30 wt %) | 3.5 | 5 (0.62 g/69 wt %) | 3 (0.01 g/1 wt %) | 2 (2.09 g/70 wt %) | 20 ppm | 0.90 | Yes |
| 41 | 5 (0.20 g/22 wt %) | 3.5 | 5 (0.68 g/76 wt %) | 3 (0.02 g/2 wt %) | 2 (2.09 g/70 wt %) | 20 ppm | 0.90 | Yes |
| 42 | 5 (0.11 g/12 wt %) | 3.5 | 5 (0.76 g/85 wt %) | 3 (0.03 g/3 wt %) | 2 (2.09 g/70 wt %) | 20 ppm | 0.90 | Yes |
| 43 | 5 (0.05 g/5 wt %) | 3.5 | 5 (0.82 g/90 wt %) | 3 (0.04 g/5 wt %) | 2 (2.09 g/70 wt %) | 20 ppm | 0.90 | Yes |
| 44 | 5 (0.17 g/9 wt %) | 3.5 | 5 (0.57 g/62 wt %) | 5 (0.17 g/19 wt %) | 2 (2.09 g/70 wt %) | 20 ppm | 0.90 | Yes |
| 45 | 5 (0.17 g/19 wt %) | 3.5 | 5 (0.57 g/62 wt %) | 5 (0.17 g/19 wt %) | 3 (2.09 g/70 wt %) | 20 ppm | 0.90 | Yes |
| 46 | 5 (0.10 g/11 wt %) | 3.5 | 5 (0.29 g/32 wt %) | 2 (0.52 g/57 wt %) | 2 (2.09 g/70 wt %) | 20 ppm | 0.90 | Yes |
| 47 | 5 (0.18 g/20 wt %) | 3.5 | 5 (0.62 g/69 wt %) | 1 (0.10 g/11 wt %) | 2 (2.09 g/70 wt %) | 20 ppm | 0.90 | Yes |
| 48 | 5 (0.18 g/20 wt %) | 3.5 | 5 (0.61 g/68 wt %) | 4 (0.11 g/12 wt %) | 2 (2.09 g/70 wt %) | 20 ppm | 0.90 | Yes |
| 49 | 5 (0.18 g/20 wt %) | 3.5 | 5 (0.61 g/68 wt %) | 4 (0.11 g/12 wt %) | 3 (2.09 g/70 wt %) | 20 ppm | 0.90 | Yes |
| 50 | 5 (0.39 g/43 wt %) | 3.5 | 5 (0.33 g) +2 (0.19 g) [57 wt %] | None | 2 (2.09 g/70 wt %) | 20 ppm | 0.90 | Yes |
| 51 | 5 (0.58 g/64 wt %) | 3.5 | 7 (0.04 g) + 2 (0.28 g) [36%] | None | 2 (2.09 g/70 wt %) | 20 ppm | 0.90 | Yes |
| 52 | 5 (0.41 g/45 wt %) | 3.5 | 7 (0.06 g) + 2 (0.40 g) [51%] | 3 (0.03 g/4 wt %) | 2 (2.09 g/70 wt %) | 20 ppm | 0.90 | Yes |
| 53 | 5 (0.24 g/27 wt %) | 3.5 | 5 (0.41 g) + 2 (0.23 g) [71%] | 3 (0.02 g/2 wt %) | 2 (2.09 g/70 wt %) | 20 ppm | 0.95 | Yes |
| 54 | 6 (8.92 g/42 wt %) | 4.9 | 2 (12.08 g/58 wt %) | None | 1 (38.77 g/70 wt %) | 20 ppm | 0.95 | Yes |
| 55 | 6 (8.92 g/42 wt %) | 4.9 | 2 (12.08 g/58 wt %) | None | 2 (38.77 g/70 wt %) | 20 ppm | 0.95 | Yes |
| 56 | 7 (6.10 g/36 wt %) | 4.1 | 2 10.70 g/54 wt %) | None | 1 (42.91/70 wt %) | 25 ppm | 0.95 | Yes |
| 57 | 22 (4.9 g/37 wt %) | 4.8 | 2 (8.3 g/63 wt %) | None | 1 (46.6 g/78 wt %) | 20 ppm | 0.95 | Yes |

Coloration in Hydrosilylation

Test coloration in hydrosilylation by adding silylated polysaccharide, SiH Functional Polysiloxane 2 and xylenes according to the amounts noted below to a 40-milliliter vial. Add a polytetrafluoroethylene stir bar and heat the mixture to 70° C. while mixing. Add 150 microliters of Platinum catalyst. Continue heating the reaction for 2.5 hours.

Evaluate four different reaction products using ASTM D1209-05 to determine the APHA color value for each. The four different reaction products and the APHA Color determination are as follows:

(1) Reference=use xylenes (0.92 milliliters) and SiH Polymer (0.35 g). Run just the SiH Functional Polysiloxane 2 through reaction conditions without a terminal alkene containing reactant. Resulting APHA color=>500.

(2) Vinyl-free beta-cyclodextrin=use xylenes (0.92 milliliters), SiH Functional Polysiloxane 2 (0.25 g) and Alkenyl-Functional Polysaccharide 20 (0.20 g) as the silylated polysaccharide, which is 80 mol % silylated but with fully saturated silyl groups. Resulting APHA color=>500.

(3) 33 Mol % vinyl beta-cyclodextrin=use xylenes (0.92 milliliters), SiH Functional Polysiloxane 2 (0.25 g) and Alkenyl-Functional Polysaccharide 6 (0.20 g) as the silylated polysaccharide, which is 70 mol % silylated with 33 mol % vinyl groups. Resulting APHA color=140.

(4) 100 Mol % vinyl beta-cyclodextrin=use xylenes (0.92 milliliters), SiH Functional Polysiloxane 2 (0.36 g) and Alkenyl-Functional Polysaccharide 21 (0.09 g) as the silylated polysaccharide, which is a 75 mol % silated with 100 mol % vinyl groups. Resulting APHA color=50.

Results reveal that vinyl-functional silylated beta-cyclodextrin surprisingly achieves an APHA color of less than 500, even less than 300 after being included in a hydrosilylation reaction with a platinum catalyst.

Pastes of Elastomer Gels

Prepare pastes of gels of the crosslinked polysiloxane elastomers of the present invention and gels of common polysiloxane elastomers by subjecting the gels to shear in a blender while adding additional solvent as described below. Then characterized the resulting pastes for Sensory Properties, Durability to washing, and Solvent Compatibility.

Preparation of the Paste Samples and References

Paste Sample 1 (PS1). Shear 60.0 g of Sample 54 in a Waring model 7012 blender and gradually dilute with 17.8 g of Solvent 1. Continue mixing under shear for approximately 5-10 minutes until achieving a paste having a viscosity of 300,000 milliPascals (Brookfield DV-11 Plus Pro Programmable Viscometer with a helipath spindle (S94) at 2.5 revolutions per minute (RPM) at 25° C.).

Paste Sample 2 (PS2). Shear 60.0 g of Sample 55 in a Waring model 7012 blender and gradually dilute with 17.8 g of Solvent 2. Continue mixing under shear for approximately 5-10 minutes until achieving a paste having a viscosity of 400,000 milliPascals (Brookfield DV-11 Plus Pro Programmable Viscometer with a helipath spindle (S94) at 2.5 RPM at 25° C.).

Paste Sample 3 (PS3). Shear 56.0 g of Sample 56 in a Waring model 7012 blender and gradually dilute with 31.1 g of Solvent 1. Continue mixing under shear for approximately 5-10 minutes until achieving a paste having a viscosity of 280,000 milliPascals (Brookfield DV-11 Plus Pro Programmable Viscometer with a helipath spindle (S94) at 2.5 RPM at 25° C.).

Paste Sample 4 (PS4). Shear 1.78 g of Sample 19 in a Waring model 7012 blender and gradually dilute with 6.0 g of Solvent 1. Continue mixing under shear for approximately 5-10 minutes until achieving a paste having a viscosity of 65,000 milliPascals (Brookfield DV-11 Plus Pro Programmable Viscometer with a helipath spindle (S94) at 2.5 RPM at 25° C.).

Paste Sample 5 (PS5). Shear 57.2 g of Sample 57 in a Waring model 7012 blender and gradually dilute with 13.2 g of Solvent 1. Continue mixing under shear for approximately 5-10 minutes until achieving a paste having viscosity of 300,000 milliPascals (Brookfield DV-11 Plus Pro Programmable Viscometer with a helipath spindle (S94) at 2.5 RPM at 25° C.).

Paste Reference 1 (PR1). PR1 is a commercially available material obtainable from The Dow Chemical Company under the name DOWSIL™ 9041 Silicone Elastomer Blend.

Paste Reference 2 (PR2). PR2 is a commercially available material obtainable from The Dow Chemical Company under the name DOWSIL™ 3901 Liquid Satin Blend.

Paste Reference 3 (PR3). PR3 is a commercially available material obtainable from The Dow Chemical Company under the name DOWSIL™ EL-8040 ID Silicone Organic Blend.

Paste Reference 4 (PR4). PR4 is a commercially available material obtainable from The Dow Chemical Company under the name DOWSIL™ EL-8050 ID Silicone Organic Elastomer Blend.

Paste Reference 5 (PR5). PR5 is a commercially available material obtainable from The Dow Chemical Company under the name DOWSIL™ EL-7040 Hydro Elastomer Blend.

Paste Reference 6 (PR6). PR6 is a commercially available material obtainable from The Dow Chemical Company under the name DOWSIL™ EL-9241 DM Silicone Elastomer Blend.

Characterization of the Paste Samples and References

Characterize the Pastes with the Following Evaluations:

Sensory Evaluation. 5 panelists of people trained for sensory evaluations and who regularly participate in sensory evaluations wash their forearms, hand and fingers with 4.3 wt % active sodium lauryl ether sulfate in water, rinse with distilled water and dry using paper towels. 50 milligrams of a paste sample or past reference is applied to the inside of their forearm with a circular motion at 2 rubs per second for a maximum of 120 rubs. Panelists evaluate the following skin sensory parameters on a scale of 1 to 5:

(a) Smoothness: evaluating evenness of film and uniformity of texture (1=sand and 5=talc)

(b) Powderyness: seeking a dry, soft, smooth, slippery feel (1=petrolatum and 5=talc)

(c) Greasiness: detecting tacky dense coating associated with drag (1=talc and 5=petrolatum)

(d) Tackiness: stickiness or degree to which fingers sticks to the skin (1=untreated skin and 5=lanolin)

(e) Wetness: amount of liquid perceived after 10 rubs (1=talc and 5=mineral oil)

Evaluations were compared within each sensory attribute across all samples with a one-way ANOVA. If the p-value was $<0.05$, a post-hoc Tukey-Kramer HSD test was conducted. Samples that were statistically different at the $p<0.05$ level were indicated as being different.

TABLE 5

| Paste | Smoothness | Powderyness | Greasiness | Tackiness | Wetness |
|---|---|---|---|---|---|
| PS1 | 4.2 | 3.2 | 3.2 | 1.8 | 1.8* |
| PS2 | 3.4 | 2.4 | 3.2 | 2.4 | 2.4* |
| PS3 | 4.4 | 3.8* | 1.6 | 1.4 | 2.1* |
| PR1 | 3.8 | 2.8 | 2.8 | 2.6 | 2.0* |
| PR2 | 4.2 | 1.6 | 1.6 | 2.6 | 4.7 |

*indicates values that are statistically different from PR2 at a p-value of <0.05 according to a Tukey-Kramer HSD test.

The results in Table 5 reveal that pastes of crosslinked polysiloxane elastomers of the present invention have a sensory profile associated with typical silicone elastomer blends (PR1) but are distinct from other crosslinked silicone materials. PS3 is a sample with exemplary powderyness.

Durability Testing. Put 8 grams of paste and 2 g of Skolor Glare™ violet SG-7661E pigment (from CQV Co. Ltd.) into a dental cup and mix using a FlackTek DAC150 speed mixer at 2300 RPM for 20 seconds. Coat 0.3 grams of the resulting mixture onto a 4.75 centimeter by 5-centimeter collagen covered microscope slide. Allow the coated slide to dry at 25° C. for 24 hours. Wash the coated slide by applying a solution of 0.07 g of DIAL™ (trademark of Henkel) Dish soap in 0.07 g of water to the coated slide with a wet fingertip for 20 seconds. Capture an image of the slide and analyze using Image J software before and after washing to determine the area of material that remained. The percent of the coated area that remains coated after washing is the Durability value in Table 6—higher values correlate to higher durability.

TABLE 6

| Paste | Durability |
|---|---|
| PR1 | 0 |
| PR3 | 25 |
| PR4 | 2 |
| PS1 | 100 |
| PS5 | 91 |

TABLE 6-continued

| Paste | Durability |
|---|---|
| PS4 | 63 |
| PS2 | 25 |

The data Table 6 reveals that PR1 has poor wash durability. PR1 is a paste made with a pure silicone paste—a silicone elastomer gelled with is polysiloxane solvent. PR1 is a benchmark paste for sensory characteristics, but has poor wash durability.

The data in Table 6 further indicates that pastes of the gelled crosslinked polysiloxane elastomers of the present invention have a greater wash durability than pastes of pure silicone elastomer gels gelled with the same solvent. Comparing PR3 and PR4 (both silicone elastomers gelled with isododecane) to PS1 and PS5 (elastomer of the present invention gelled with isododecane) reveals a remarkable improvement in wash durability for the inventive elastomer.

PS4 is a paste of an elastomer of the present invention prepared as a gel in farnesane that was diluted in isododecane when the paste was made. Farnesane (boiling point of 252° C. at 101 MegaPascals pressure) is a lower volatility solvent than isododecane (boiling point of 210° C. at 101 MegaPascals pressure). Even with a lower volatility solvent added, the PS4 paste has greater wash durability than PR3 and PR4.

PS2 provides a paste of an elastomer of the present invention prepared as a gel in farnesane and diluted in farnesane when made into a paste. Even when using only a lower volatility solvent (farnesane) in making the gel and paste, the paste has a wash durability comparable to the most durable reference sample with a higher volatility solvent (isododecane).

These results demonstrate the inherently greater wash durability of pastes made with the polysaccharide-containing elastomers of the present invention as compared to conventional purely silicone elastomers.

Solvent Compatibility. Add 7.5 g of paste and 2.5 g of test solvent to a dental cup and mix using a FackTek DAC150 speed mixer at 2300 RPM for 30 seconds. Allow the samples to set undisturbed at 25° C. for 24 hours and then evaluate solvent compatibility with the following scale:

1-Clear: sample is free of haze and one can easily read through the mixture when text is placed behind it.

2-Slightly Hazy: sample is nearly clear, only a very slight haze is detectable and one can still easily read through the sample when test is placed behind it.

3-Hazy: Sample is not clear and text placed behind the sample can be perceived but not read.

4-Opaque: white solid, light cannot pass through and one cannot detect what is placed behind the sample.

5-Incompatible: sample phase separated.

TABLE 7

| | Solvent | | | | |
|---|---|---|---|---|---|
| Paste | Ethylhexyl-methoxy cinnamate | C12-C15 alkyl benzoate | Caprylic/carpic triglyceride | XIAMETER ™ PMX-200 Silicone Fluid (2cSt) | PPG-3 Myristyl Ether |
| PS2 | 3 | 1 | 1 | 1 | 1 |
| PS3 | 3 | 1 | 1 | 3 | 1 |
| PR1 | 5 | 3 | 3 | 2 | 3 |
| PR3 | 3 | 2 | 2 | 1 | 2 |

The data in Table 7 reveals that pastes of gels from the crosslinked polysiloxane elastomer of the present invention is greater solvent compatibility over a broader range of solvents than pastes of the reference polysiloxanes.

Hydrolytic Instability of C—O—Si Bond Versus C—O—C Bond

Samples (15 mg) were placed into a glass NMR tube in 0.6 mL of either d6-acetone (Sample 23) or d6-DMSO (Polysaccharide 7). Then, 5 μL of a 9:1 v/v solution of water/trifluoroacetic acid was added, and 1H NMR spectra were acquired at the timepoints in Table 8. The Mol % C—O—Si hydrolysis was measured by integrating TMS-cyclodextrin peaks from δ 0.1-0.3 ppm and hydrolyzed TMS groups from δ 0.03-0.07 ppm. The Mol % C—O—C hydrolysis was determined by evaluating C—O—$CH_3$ as determined by assessing growth of any resonances of MeOH, present at δ 3.31 in d6-acetone and δ 3.16 in d6-DMSO. After the 5h time point for sample 23, a white precipitate was observed in the NMR tube. The precipitate was isolated by evaporating volatiles. The precipitate was soluble in d6-DMSO and analyzed to be consistent with the starting material, Polysaccharide 7.

TABLE 8

| Sample | Time (h) | Mol % C—O—Si Hydrolysis | Mol % —C—O—C Hydrolysis |
|---|---|---|---|
| 23 | 0 | 3 | 0 |
| 23 | 0.5 | 13 | 0 |
| 23 | 5 | 84 | 0 |
| Polysaccharide 7 | 0 | N/A | 0 |
| Polysaccharide 7 | 3 | N/A | 0 |

Sample 23 shows an increase in the amount of hydrolyzed C—O—Si bonds over time, increasing from 3% hydrolyzed at time 0 (due to residual byproduct from the synthesis reaction) to 84% hydrolyzed after 5 hours at room temperature. The methyl groups from that sample forming C—O—C bond, however, remain intact and do not show any evidence of hydrolysis. As a control case, a pristine sample of methyl-beta-cyclodextrin was also treated with trifluoroacetic acid as above. This sample also did not show any degradation of the C—O—C groups after 3 hours at room temperature demonstrating the stability of this bond.

The data affirms a lower hydrolytic stability of C—O—Si bonds relative to the C—O—C bonds.

Hydrophilicity of Samples

Evaluate the hydrophilicity of paste samples using contact angle measurements. Apply the paste samples in a uniform film to a 3"×2" glass microscope slide using a 50 micrometer film applicator. Then, place 8 microliter droplet of ultrapure (>18 M-ohm centimeter) water on top of the film with a micropipette. Measure the contact angle of the droplets on the film with an AST Products VCA Optima video contact angle system. VCA-2500XE software was utilized to calculate the contact angle. Contact angles below 90 degrees)(° indicate a hydrophilic film.

TABLE 9

| Paste Sample | Contact Angle (°) | Hydrophobic/ Hydrophilic |
|---|---|---|
| PS1 | 103 | Hydrophobic |
| PS3 | 94 | Hydrophobic |

TABLE 9-continued

| Paste Sample | Contact Angle (°) | Hydrophobic/ Hydrophilic |
|---|---|---|
| PR5 | 58 | Hydrophilic |
| PR6 | 103 | Hydrophobic |

What is claimed is:

1. A composition comprising a crosslinked polysiloxane elastomer comprising 2 or more carbon-oxygen-silicon linkages between a polysaccharide component and polysiloxane component, where the polysaccharide component is other than a cellulose or starch component and where the composition is a gel comprising the crosslinked polysiloxane elastomer swollen with a solvent and is in a form of a paste resulting from subjecting the gel to shear mixing.

2. The composition of claim 1, wherein the polysaccharide component comprises fructose, galactose, anhydrogalactose or glucose linked saccharide units provided that glycosidic linkages of glucose are alpha linkages.

3. The composition claim 1, wherein the polysaccharide component only has pendant groups other than the linkage to the polysiloxane that are selected from a group consisting of —$OSiR_3$ groups, —$CH_2OSiR_3$ groups, —OH and —$CH_2OH$.

4. The composition of claim 1, wherein the polysaccharide component is selected from a group consisting of beta-cyclodextrin, maltodextrin, pullulan, dextran, trehalose, inulin, and agarose.

5. The composition of claim 1, wherein each polysaccharide component comprises on average 2 to 2000 linked saccharide units.

6. The composition of claim 1, wherein the solvent is one or more solvent selected from isododecane, farnesane, undecane, n-dodecane, and tridecane.

7. A method for preparing the composition of claim 1, the method comprising forming the crosslinked polysiloxane elastomer by a hydrosilylation addition reaction between reactants comprising:

(a) a SiH functional polyorganosiloxane that has an average of at least two SiH functionalities per molecule;

(b) an alkenyl-functional polysaccharide that is characterized by:

(i) comprising linked fructose, galactose, anhydrogalactose, or glucose saccharide units provided that glycosidic linkages of glucose are alpha linkages;

(ii) on average one to 100 mole-percent of the hydroxyl groups on the alkenyl-function polysaccharide have been silylated with a silyl group having the structure —$SiR_3$ linked to the polysaccharide through a C—O—Si bond where each R is independently selected from hydrocarbyl radicals having from one to 12 carbon atoms, provided that on average at least 2.0 R groups per polysaccharide are terminal alkenyl groups; and (iii) that the alkenyl-functional polysaccharide is other than a cellulose or starch component; and (c) optionally, additional crosslinking additives;

where the reaction is run in the presence of:

(d) a platinum-based hydrosilylation catalyst; and (e) a solvent, and then subjecting the resulting crosslinked polysiloxane elastomer gel to shear mixing to form a paste.

8. The method of claim 7, wherein the alkenyl-functional polysaccharide is selected from a group consisting of silylated beta-cyclodextrin, silylated maltodextrin, silylated pullulan, silylated dextran, silylated trehalose, silylated inulin, and silylated agarose.

9. The method of claim 7, wherein the concentration of solvent is 30 wt % or more and 85 wt % or less of the combined weight of SiH functional polysiloxane, alkenyl-functional polysiloxane and organic solvent.

* * * * *